United States Patent [19]
Katz et al.

[11] Patent Number: 5,925,669
[45] Date of Patent: Jul. 20, 1999

[54] CARRIER COMPOSITIONS FOR ANTI-NEOPLASTIC DRUGS

[75] Inventors: Robert Katz, Gaithersburg; Maria Tomoaia-Cottsel, Rockville, both of Md.

[73] Assignee: Molecular/Structural Bio Technologies, Inc., Bethesda, Md.

[21] Appl. No.: 08/503,326

[22] Filed: Jul. 17, 1995

Related U.S. Application Data

[63] Continuation-in-part of application No. 08/218,898, Mar. 22, 1994, abandoned.

[51] Int. Cl.⁶ .......... A61K 31/335; A61K 31/70; A61K 31/20; A61K 33/24
[52] U.S. Cl. ............ 514/449; 514/34; 514/558; 424/649
[58] Field of Search .................. 514/449, 560, 514/558, 34; 424/649

Primary Examiner—Jerome D. Goldberg
Attorney, Agent, or Firm—Isaac A. Angres

[57] ABSTRACT

The invention provides new carrier compositions containing a triglyceridic oil rich in DHA and anti-neoplastic drugs and a DHA-containing phospholipid.

5 Claims, No Drawings

CARRIER COMPOSITIONS FOR ANTI-NEOPLASTIC DRUGS

This application is a continuation-in-part of application Ser. No. 08/218,898 filed Mar. 22, 1994, abandoned.

FIELD OF THE INVENTION

The present invention relates to therapies for the treatment of malignant neoplasms and their prevention with natural or synthetic oils having substantial levels of docosahexaenoic acid. The instant invention also relates to pharmaceutical compositions containing oils having high levels of docosahexaenoic acid and antineoplastic drugs.

BACKGROUND OF THE INVENTION

Omega-3 (n-3) polyunsaturated fatty acids (PUFA), such as alpha-linolenic acid (ALA orC18:3,n-3), eicosapentaenoic acid (EPA or C20:5,n-3), docosapentaenoic acid (DPA or C22:5,n-3) and docosahexaenoic acid (DHA,C22:6, n-3) are major components of cellular membranes with an ever-increasing array of newly discovered physiologic roles such as: maintenance of membrane flexibility, modulation of autoimmunity, inhibition of inflamation and platelet aggregation, reduction of hypertriglyceridemia,inhibition of neoplastic cell proliferation and metastasis. ALA is available from plants, e.g., flax seed and rape seed or canola oils, and some vegetables (e,g,. purslane and spinach). It serves as a catabolic precursor for EPA (1) and DHA (2), which are available for human consumption mainly from marine sources. The ALA to EPA to DHA tamsformation is slow and an in vivo production of 0.3 grams of EPA requires ingestion of about 3.0 grams of ALA. Therefore, marine sources, consisting mainly of oil of cold water fish (menhaden, tuna, salmon, cod, etc.) are used to shortcut the tedious metabolic pathway and provide the organism with the needed PUFA.

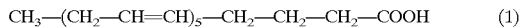

$$CH_3-(CH_2-CH=CH)_5-CH_2-CH_2-CH_2-COOH \quad (1)$$

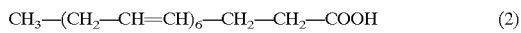

$$CH_3-(CH_2-CH=CH)_6-CH_2-CH_2-COOH \quad (2)$$

Such cold-water fish oils provide a mixture of omega-3s, containing EPA (up to about 15% of total fatty acids by weight) and DHA (up to about 12% of total fatty acids by weight) were the main source of omega-3 PUFA The refining, deodorization and purification of these oils, or their individual fatty acid components, for human therapeutic use are tedious and expensive processes.

The EPA and DHA in these processed oils are highly oxidation-sensitive if exposed to air. The unpleasant fish odor of the oil returns, even with addition of antioxidants like alpha-tocopherol (vitamin E). DHA is the less oxidation-sensitive of the two PUFA, and its encapsulation under nitrogen ensures a reasonable shelf life. It appears that the more DHA and the less EPA are present in an oil, the more stable the oil becomes and its shelf life is prolonged.

Recently, two new, natural sources of DHA-rich oils, with a preponderance of DHA-containing mixed triglycerides, have been identified and developed: 1) oil from the ocular orbit fatty tissue of tuna, which provides an odorless source of at least 27% DHA of total fatty acids by weight and only about 7–8% EPA. This oil, sold in the United States under the trade name DHA Maguro, requires only minimum processing under nitrogen, at low temperatures, and. 2) oils from algae and algae-like microorganisms that provide odorless oils that contain up to 50% DHA, are free of EPA or contain only small amounts of EPA and essentially no other polyunsaturated fatty acids (W. R. Barclay, K. M. Meager, and J. R. Abril, "Heterotrophic production of long chain omega-3 fatty acids utilizing algae and algae-like microorganisms," J. Appl. Phycology, 1994, 6, 123–129). The pharmaceutical utility of these oils can be enhanced through control of the biotechnologic fermentation process and its degree of sterility. These oils can be further enriched with docosahexaenoylethylester and/or various docosahexaenoyl-containing phospholipids such as: 1-stearoyl, 2-docosahexaenoyl phosphatidylcholine or 1-stearoyl, 2-docosahexaenoyl phosphatidyl ethanolamine.

The present invention is building on the availability of these odorless, easy to sterilize high-DHA content triglyceride-based oils for the theraeutic applications described herewithin.

The understanding of the role of PUFA, particularly EPA and DHA and their esters with alkanols and glycerol in therapeutic applications related to cancer such as prevention of cancers, inhibition of tumor growth and prevention of dissemination of cancer cells (metastases) is steadily increasing [ Spector, A. A., and Bums, C. P., "Biological and therapeutic potential of membrane lipid modification in tumors," Cancer Res., 1987, 47, 4529–4537; Rose, D. P. and Cohen, L. A., "Effects of dietary menhaden oil and retinyl acetate on the growth of DU 145 human prostatic adenocarcinoma cells transplanted into athymic nude mice," Carcinogenesis, 1998, vol.9, no.4, 603–605; Bums, CP., and Spector, A. A, "Effects of lipids on cancer therapy," Nutr. Rev., 1990, vol. 48, no.6, 233–240; Lowell, J. A., Pames, H. L., and Blackburn, G. L., "Dietary immunomodulation: beneficial effects on oncogenesis and tumor growth," Crit. Care Med., 1990, 18(2 Suppl): S145–8; Grunfeld, C., and Feingold, K. R., "Tumor necrosis factor, interleukin, and interferon induced changes in lipid metabolism as part of host defense," Proc. Soc. Exp. Biol. Med., 1992, 200(2): 224–7; De Vries, C. E., and van Noorden, C.,J., "Effects of dietary fatty acid composition on tumor growth and metastasis," Anticancer Res., 1992, 12(5):1513–22; Isffan, N. W., Wan, J. M., and Bistrian, B. R., "Nutrition and tumor promotion: in vivo methods for measurement of cellular proliferation and protein metabolism," J. Parenter. Enteral. Nutr., 1992, 16(6 Suppl): 76–82S; Kinsella, J. E., and Black, J. M., "Effects of polyunsaturated fatty acids on the efficacy of antineoplastic agents toward L5178Y lymphoma cells," Biochem. Pharm., vol. 45, no. 9, 1881–1887; Connolly, J. M., and Rose, D. P., "Effects of fatty acids on invasion through reconstituted basement membrane ('Matrigel') by a human breast cancer cell line," Cancer Letters 1993, 75, 137–142; Gonzalez, M. J., et al., "Dietary fish oil inhibits human breast carcinoma growth: a function of increased lipid peroxidation," Lipids, vol.28, no.9, 827–832; Rose, D. P., and Connolly, J. M., "Effects of dietary omega-3 fatty acids on human breast cancer growth and metastases in nude mice," J. Nat. Cancer Inst. 1993, 85 (21), 1743–47].

Very recent data from a study aimed at comparing three concentrated n-3 PUFA preparations-ethyl esters, free fatty acids and re-esterified triglycerides-with placebo oil in a double-blinded study showed that the bioavailability of orally administered EPA and DHA, from highly concentrated preparations containing EPA and DHA as re-esterified triglycerides, was significantly better than ethyl esters and even better than free acids. (Kilde: Dyerberg J. "Bioavailability of n-3 fatty acids formulations". European Society for Clinical Investigation, Annual Meeting April, 1995. Workshop: Preventive Strategies in Vascular Disease: Focus on n-3 Fatty Acids). Additional data indicates that specific triacyl glycerols with EPA and DHA in the 2-(sn2) position of glycerol, provides a readily absorbed source of long chain omega-3 PUFA for nutritional supplementation purposes. (Christensen, M. S., et al, "Intestinal absorption and limphatic transport of eicosapentaenoic (EPA), docosahexaenoic (DHA), and decanoic acids: dependence on intramolecular triacylglycerol structures", Am. J. Clin. Nutr. 1995, 61, 56–61.)

In prior art. DHA was tested to determine its mode of action as an anticancer agent. It is shown that DHA, either as the free fatty acid or as 1-stearoyl-2-docosahexaenoyl-sn-glycero-3-phosphocholine, is incorporated in tumor plasma membranes (e.g. T27A leukemia cell membranes) and makes them substantially more permeable, explaning at least in part its anti-tumor properties. [For details, see Stillwell W., Ehringer W. and Jensid L. J., "Docosahexaenoic acid increases permeability of lipid vesicles and tumor cells", Lipids 1993, 28(2): 103–8; Jenski L. J., Sturdevant L. K., Ehringer, W. D., and Stillwell W., "Omega-3 fatty acid modification of membrane structure and function. I. Dietary manipulation of tumor call susceptibility to cell- and complement-mediated lysis", Nutr. Cancer 1993, 19(2): 135–46; Pascale A. W., Ehringer, W. D., Stillwell W., Sturdevant L. K., and Jenski L. J., "Omega3 fatty acid modification of membrane structure and function. II. Alteration by docosahexaenoic acid of tumor cell sensitivity to immune cytolysis", Nutr. Cancer 1993, 19(2): 147–57].

Docosahexaenoic acid has an inhibiting effect on tumor growth. Lipid peroxidation appears to be an important factor in the inhibition of tumor growth. Both EPA and DHA seem to autooxidize enzymatically by cytochrome P450, cyclooxygenase and lipoxygenase. For example, DHA in 1-oleoyl 2-docosahexaenoyl-sn glycero3-phosphocholine (1-oleoyl 2-DHA-PC) was found to be a potent inhibitor of 5-lipoxygenase [Matsumoto K, Morita I., Hibino H. and Murota S., "Inhibitory effect of docosahexaenoic acid-containing phospholipids on 5 lipcxygenase in rat basophilic leukemia cells", Prostaglandins Leukot Essent Fatty Acids 1993, 49(5): 861–6].

In vitro studies demonstrated that docosahexaenoic acid is cytotoxic at concentrations greater than or equal to 20 microM after 48–72 h in culture. The extension of these results to situations in vivo could lead to use of docosahexaenoic acid for delaying leukemia progression or in adjuvant chemotherapy [Anel A., Naval J., Desportes P., Gonzalez B., Uriel J., and Pineiro A., "Increased cytotoxicity of polyunsaturated fatty acids on human tumoral B and T-cell lines compared with normal lymphocytes", Leukemia, 1992, 6(7): 680–8].

Also, omega-3 fatty acids (mainly DHA) inhibited MDA-MB-435 human breast cancer cell line invasion in vitro [as demonstrated by Connolly J. M. and Rose D. P., "Effects of fatty acids on invasion through reconstituted basement membrane ('Matrigel') by a human breast cancer cell line", Cancer Lett, 1993, 75(2): 137–42].

The roles of DHA in inhibition of growth and metastasis of murine transplantable mammary tumor have been recently described [Kinoshita K., Noguchi M., Earashi M., Tanaka M. and Sasaki T., "Inhibitory effects of purified eicosapentaenoic acid and docosahexaenoic acid on growth and metastasis of murine transplantable mammary tumor", In vivo, 1994, 8 (3): 371–4].

The growth and sensitivity of neoplastic cells to chemotherapeutic agents may be altered by the type of fatty acids incorporated in cell membranes. For example, a prior enrichment of cellular components with DHA enhances the toxic action of anticancer drugs [Kinsella J. E., and Mark Black J., "Effects of polyunsaturated fatty acids on the efficacy of antineoplastic agents toward L5178Y lymphoma cells", Biochem. Pharmacology, 1993, 45(9), 1881–1887; Wagner B. A., Buettner G. R., and Burns C. P., "Increased generation of lipid-derived and asoorbate free radicals by L1210 cells exposed to the ether lipid edelfosine", Cancer Res., 1993, 53: 711–713; Buettner G. R., Kelley E. E., and Burns, C. P., "Membrane lipid free radicals produced from L1210 murine leukemia cells by photofrin photosensitization: An electron paramagnetic resonance spin trapping study", Cancer Res., 1993, 53:3670–3673; Petersen E. S., Kelley E. E., Modest E. J., and Burns C. P., "Membrane lipid modification and sensitivity of leukemic cells to the thioether lipid analogue BM 41.440", Cancer Res., 1992, 52: 6263–6269].

A recent series of studies indicated that DHA containing diacyl- and alkenylacylglycerophosphoethanolamine (DHA-diacylGPE, and DHA-alkenyl acyGPE) are not susceptible to deacylation and release of the DHA by the cytosolic phospholipase A2 (cPLA2). This behaviour was in stark contrast with the behavior of arachidonic acid- and EPA-containing diacylGPE and alkenylacyGPE derivatives. The authors assume that clear discrimination of DHA from EPA and archidonic acid by cPLA2, may provide a new basis for understanding the beneficial effects of DHA. [Shikano, M., Masuzawa Y., Yazawa K., Takayama K., Kudo I., and Inoue K., "Complete discrimination of docosahexaenoate from arachidonate by 85 kDa cytosolic phospholipase $A_2$ during the hydrolysis of diacyl- and alkenylacylglycerophosphoethanolamine", Biochin Biophys. Acta, 1994, 1212:211–216].

Another study found that DHA is incorporated more readily into malignant brain tumour tissue (e.g. glial tumours, astrocytomas and glioblastomas) than into normal brain tissue due primarily to an increased utilization of fatty acids by tumor cells [Nariai T., Greig N. H., DeGeorge J. J., Genka S. and Rapoport S. I., "Intravenously injected radio-labelled fatty acids image brain tumour phospholipids in vivo: differential uptakes of palmitate, arachidonate and docosahexaenoate", Clin. Exp. Metastasis, 1993, 11:141–149].

Recently, is shown that DHA suppresses the formation and growth of colon cancer and has a preventive effect on colon carcinogenesis [Takahashi M., Minamoto T., Yamashita N., Yazawa K, Sugimura T., and Esumi H., "Reduction in formation and growth of 1,2-dimethylhydrazine-induced aberrant crypt foci in rat colon by docosahexaenoic acid", Cancer Res., 1993, 53 (12): 2786–9; Anti M., Marra G., Armelao, F., Bartoli G. M., Ficarelli R., Percesepe, A, De Vitis I., Maria G., Sofo L., Rapaccini G. L., et al., "Effect of omega-3 fatty acids on rectal mucosal cael proliferation in subjects at risk for colon cancer", Gastroenterology 1992, 103(3), 883–91; Gastroenterology 1993, 104(4):1239–41].

It was recently emphasised that the intestinal absorption and lymphatic transport of DHA depends on intramolecular triacylglycerol structure. Specific triacylglycerols with DHA in the sn-2 position and medium-chain saturated acyl substituents in the sn-1 and sn-3 positions of are of value in delivering DHA and in ensuring adequate bioavailability following enteral administration. Interesterified or re-esterified triacylglycerols open new possibilities for designing special lipids for particular therapeutic purposes. [Christensen M. S., Hoy C. E., Becker C. C. and Redgrave T. G., "Intestinal absorption and lymphatic transport of eicosapentaenoic (EPA), docosahexaenoic (DHA), and decanoic acids: dependence on intramolecular triacylglycerol structure", Am. J. Clin. Nutr., 1995, 61: 56–61; Specific and random triglicerides are described in U.S. Pat. Nos. 5,227,403, July, 1993 Seto et al.: Fats and oils having superior digestibility and absorptivity used as nutrients; and 4,701,469 October, 1987 Mendy et al., Preparation, dietetic applications and compositions of specific triglycerides.]

Another recent study of arachidonic acid metabolism in benign and malignant prostatic tissue, related the presense of high levels of prostaglandin E2 (PGE2) in the malignant prostatic tissue (as opposed to cells from benign prostatic hyperplasia patients, and normal subjects). Since arachidonic acid is responsible for PGE2 formation as well as diacyl glycerol (DAG) formation in the neoplastic malignant cells and omega-3 PUFAs from fish oil significantly inhibited PGE2 and DAG formation in the neoplastic cells, it is reasonable to assume that either EPA, or DHA or both present in the fish oil exhibit possible therapeutic effectc in human prostate cancer.

Significant increase in survival of T27A murine leukemia cell-containing, tumor-bearing mice was reported when the mice were treated intraperitoneally with small unilamellar vesicle preparations of 1-stearoyl, 2-docosahexaenoyl phosphatidylcholine. Although a positive effect was observed also with the derivative in which alpha-linolenic acid replaced docosahexaenoic acid, the strongest survival effect was that of the DHA derivative. (Jenski, L. J. et al., "Antitumor effects of omega-3 fatty acid-containing lipid vesicles administerd in situ". Abstract #134, 2nd International Congress of the ISSFAL International Society for the Study of Fatty Acids and Lipids, Jun. 7–10, 1995, NIH Bethesda Md., on "Fatty Acids and Lipids From Cell Biology To Human Disease"). The prior art is silent regarding the use of DHA rich triglyceridic oils in treating neoplastic diseases.

OBJECTS OF THE INVENTION

An important object of the present invention is a method for treating or preventing malignant neoplasms with oils having high levels of docosahexaenoic acid.

An additional object of the present invention is a method for treating lung neoplasms with an oil having high levels of docosahexaenoic acid..

A further object of the invention is a method for treating prostatic neoplasms with an oil having high levels of docosahexaenoic acid.

A still additional object of the invention is the treatment of brain cancers with an oil having high levels of docosahexaenoic acid.

Another object of the invention is a method for treating malignant tumors of the breast with an oil having high levels of docosahexaenoic acid.

A further objective of the present invention is the treatment of colon cancer with an oil having high levels of docosahexaenoic acid.

Still another object of the invention is a method for treating leukemias with an oil having high levels of docosahexaenoic acid.

A still further object of the invention is to provide therapeutic compositions for the treatment of malignant neoplasms which contain an oil having high levels of docosahexaenoic acid and an antitumor drug.

Yet another object of the invention is to provide pharmaceutical compositions with enhanced therapeutic effect (e.g., liposomal or micellar dispersions emulsions, or encapsulated drugs, etc.) made from said oil and lipids containing high levels of docosahexaenoic acid.

Another important aspect of the invention is the use of oils having 15%–100% by weight of docosahexaenoic acid as therapeutic agents for malignant neoplasms.

Another important aspect of the invention is the treatment of prostatic carcinomas with an oil having 15%–100% by weight of docosahexaenoic acid.

Other important aspects of the instant invention will be further elaborated in the preferred embodiments section of the present patent specification.

SUMMARY OF THE INVENTION

According to this invention, a method is provided for treating malignant neoplasms in a mammal which comprises administering to said mammal an effective antineoplastic amount of an oil having high levels of docosahexaenoic acid (DHA). More specifically, oils having high levels of docosahexaenoic acid inhibit the proliferation of malignant cells, control the growth of malignant neoplasms, reduce the size of malignant neoplasms, prevent malignant neoplasms, eradicate malignant neoplasms, prolong remission time and the survival time of said mammal, kill malignant cells and adversely affects malignant cells.

Furthermore and according to this invention, oils having high content of docosahexaenoic acid are used as a carrier material for antineoplastic drugs such as taxol, cyclophosphamide, cis-platinum, doxorubicin, methotrexate, vincristine, 5-fluorouracyl, etc.

In simple chemical means, the oils of the present invention are natural or synthetic glycerol derivatives containing the docosahexaenoyl group at levels between 25% and 100% by weight based on the total fatty acid content.

DESCRIPTION OF THE PREFERRED EMBODIMENTS

The present invention is directed to methods for treating a malignant neoplasm (within the context of the present invention the words neoplasm and tumor are used interchangeably and are intended to have the same meaning) in a mammal in need thereof which comprises administering to said mammal an antineoplastic effective amount of a triglyceridic oil having at least 15% by weight of docosahexaenoic acid based on the total fatty acid content and no more than 10% by weight of eicosapentaenoic acid based on the total fatty acid content.

The instant invention is also directed to a method for treating and/or preventing a malignant neoplasm selected from the group consisting of lung and, breast neoplasms, prostatic carcinoma, colon cancer, leukemia and brain cancers in a mammal in need thereof which comprises administering to said mammal an antineoplastic effective amount of a triglyceridic oil having at least 15% by weight of docosahexaenoic acid based on the total fatty acid content and no more than 10% by weight of eicosapentaenoic acid based on the total fatty acid content.

A particular desirable oil for practicing the therapeutic method of the present invention is an oil derived from marine microalgae and marketed by MARTEK Biosciences Corporation (Columbia, Md.) under the name of DHASCO. The oil marketed under the name of DHASCO has 48% by weight of docosahexaenoic acid; 2% by weight of $C_{12}$ saturated fatty acid; 15.0% by weight of $C_{14}$ saturated fatty acid 20.0% by weight of $C_{16}$ saturated fatty acid; 1% by weight of $C_{18}$ saturated fatty acid and 10.0% by weight of $C_{18}$ monounsaturated fatty acid.

Other oils which have the following percent by weight formulations may be used:

$C_{12}$ saturated acid 0–5.0%

$C_{14}$ saturated acid 0–20.0%

$C_{16}$ saturated acid 0–30.0%
$C_{18}$ saturated acid 0–5.0%
$C_{18}$ monounsaturated acid 0–15.0%
$C_{20}$ eicosapentaenoic 0–10.0%
$C_{22}$ docosahexaenoic acid 15.0%–100%

It is to be understood that the oils of the present invention may also contain additional fatty acids which usually occur in oils of marine or fish origin, however they do not materially affect the effectiveness of the oils of the present invention. Other alternate oils of algal origin include those manufactured by OmegaTech of Boulder, Colo. and Kelco of San Diego, Calif. An additonal useful oil includes DHA Maguro marketed by Daito Enterprises of Los Angeles, Calif.

In another aspect of the invention, oils rich in docosohexaenoic acid are used as carriers for administering antineoplastic drugs. The preferred oil used as carrier for the antineoplastic drugs is DHASCO described above as containing 48.0% by weight of docosahexaenoic acid. The oil which is derived from marine microalgae is rich in docosahexaenoic acid and has virtually no other bioacitve polyunsaturated fatty acid as described in the Martek Biosciences Corp. product literature.

The preferred antineoplastic drugs which are formulated with oils rich in docosahexaenoic acid (DHA) include Rifamycin, busulfan, chlorambuck, cyclophosphamide, mechlorethamide hydrochloride, melphalan, pipobroman, thiotepa, uracil mustard, cytarabine, fluorouracil, floxuridine, mercaptopurine, methotrexate, thioguanine, dacarvazine, hydroxy-urea, mitotane, procarbazine hydrochloride, quinacrine hydrochloride, vinblastine sulfate, vincristine sulfate, estrogens such as methyltestosterone, testosterone, progestagens such as megestrol, hydroxyprogesterone etc. Preferred antineoplastic materials include, cis-platinum, doxorubicin, taxol, bleomycin sulfate and lipid conjugates. Suitable methods of administration, compositions and dosages of the antineoplastic agents are described in medical textbooks; for instance "Physicians Desk References" 44th edition; AMA Drug Evaluation, 3rd edition pp 1106–1151 (1977) by PSG Publishing Co., Littleton, Mass.

The oils of the present invention when used in therapy alone or as carrier for other antineoplastic drugs can be modified by standard chemical means i.e., transesterified so as to make phospholipid derivatives having high content of docosahexaenoic acid moiety. Other materials which are useful are docosahexaenoyl ethylester and 1-stearoyl-2-docosahexaenoyl-3-glycero-phosphocholine (SDHPC).

When using the oils of the present invention as carriers, the drug is dispersed in the oil alone or with the aid of additional surface active agents under conditions of high shear so as to create a uniform dispersion. When appropriate the oils can be further modified so as to make phospholipid derivatives which then can be used to make highly useful liposomes for encapsulating the antineoplastic drug.

For purposes of making liposomes, the oils of the present invention may be modified with phosphatidyl choline, phosphatidyl ethanol amines, phosphatidyl serines and phosphatidyl inositols to give suitable derivatives. A suitable derivative would be 1-stearoyl-2-docosahexaenoyl-3n-glycerophosphocholine (SDHPC).

The compositon of the invention i.e., the oils having high content of docosahexaenoic acid alone, or in combination with other antineoplastic drugs may be made up in various forms adapted to the method of adminstration, for example oral, enteral, rectal, parenteral, nebulizer or organ directed infusion. For example, they may be made up in the form of capsules, gelatin-coated pills, suppositories or syrups. In the case of enteral or parenteral administration, the compositions are formulated as nonpyrogenic and sterile, physically and chemically stable solutions or emulsions.

The dose administered depends on the type and seriousness of the disease to be treated. Effective quantities may be from 1 g to 100 g of the oil and preferably from 5 g to 10 g of the oil per day in single dose or preferably in 2 to 3 separate doses. It should be noted that the preferred oils of the invention are typically stabilized against oxidation by adding anti-oxidants such as β-carotene α-tocopherol and astaxanthin. When the drug is infused intravenously a continuous infusion might be desired over a ten hour period.

The components of a pharmaceutical composition were chosen based on their proposed effects on tumor cells, e.g. membrane structure, permeability and fluidity and on their transport efficiency in living tissues. For instance, the bioavailability of any anti-cancer regular drug is enhanced in the presence of DHA enriched oils (DHA-oils) in pharmaceutical compositions. A preservative is incorporated into pharmaceutical preparations. For example, a-tocopherol or a pharmacologically acceptable analog, derivative or ester thereof, b-carotene or other pharmacologically acceptable carotenoids and retinoids in a concentration between about 0.1%, 1% to 2% by weight are found suitable for the purposes of the present invention.

The pharmaceutical compositions according to the goals of this invention are conveniently in a form suitable for parenteral, oral, rectal and topical administration in a suitable pharmaceutical preparation, as given in any case and very well known generally for any particular type of preparation (see, U.S. Pharmacopeia:(USP)). Thus for instance capsules, tablets, ingestible preparations (e.g. emulsions or powders), salves, creams and lotions for topical applications or suppositories as well as fluids for parenteral administration can be prepared as required. The absolute amount of any active ingredient present in any dosage unit should be adequate to allow the desired administration to be achieved by a small number of doses. The rate of administration is dependent on the precise pharmacological action desired. Doses for DHA-oils are between 1 g to 100 g per day, preferably 5 g to 10 g per day, conveniently in gelatine capsules or in conventional parenteral fluids.

To further illustrate this invention, and not by way of limitation, the following specific examples are given.
Sources of DHA enriched oils, DHA and other DHA-derivatives Conventional sources of DHA include DHASCO-oil (Martek Biosciences), containing between about 25% to 100% DHA in its fatty acd composido (expressed in weight %, and symbolized for example by 25% DHA-oil to 100% DHA oil) and any highly purified or modified oil from marine or fish which contains a substantial amount of DHA (wt %), from 15% to 100% (i.e. 15% DHA-oil or 100% DHA-oil). Also, suitable physiologically functional DHA-derivatives, convertible in the body to DHA, can be used; examples of such compounds include physiologically acoeptable salts, esters (glycerides, $C_1$–$C_4$ alkyl esters), amides and phospholipids.

EXAMPLES FOR PHARMACEUTICAL COMPOSITIONS

Example for a salve:

5 g of an oil sold by Martek Biosciences under the name of DHASCO are suspended in 35 g of very viscous paraffin, 30 g of a cetyl or stearyl alcohol emulsifier and 30 g white vaseline are added thereto and melted. This melt is stirred until cold. A homogeneous active material distribution is achieved by working up of the cooled melt by means of three roll mill. 1 g of salve contains approximately 50 mg of DHASCO.

Example for Capsules 1.25 Kg of DHASCO are first dissolved in 5 Kg of chloroform and then 1.25 Kg aerosil are suspended in this solution. The solvent is stripped of in a vacuum. The dry mass is passed through a 1 mm sieve and again vacuum dried. The resulting granulate is filled in known manner on a suitable capsuling machine into hard gelatin capsules of a size containing 500 mg of granulate. Accordingly, one capsule contains 250 mg of DHASCO.

Example for Emulsion

In a suitable vessel, 1.0 to 2.0 kg of an oil derived from marine microalgae known as DHASCO (Martek Biosciences Corp) and containing 40% to 50% docosahexaenoic acid; 120 g of purified egg phospholipids, 225 g of glycerol USP and water for injection USP are mixed to produce an emulsion having a 2.25% glycerol concentration. This emulsion is then homogenized repeatedly at high pressure to produce an emulsion of mean particle diameter is adjusted to a physiological range with sodium hydroxide. The final volume is adjusted, if necessary with water for injection, USP, to 10 liters, and the emulsion is filtered into glass containers and heat sterilized.

ADDITIONAL EXAMPLES

Example 1

A salve containing 5 g of an DHA-oil, sold by Martek Biosciences under the name of DHASCO, suspended in 35 g of very viscous paraffin, 30 g of catyl or stearyl alcohol and 30 g white vaseline is prepared in a known traditional way. 1 g of salve contains approximately an amount of 50 mg oil DHASCO, enriched in DHA

Example 2

A 2 g capsule containing 500 mg of 25% DHA-oil, taken four per day.

Example 3

A 2.5 g capsule containing 500 mg of 50% DHA-oil, taken six per day.

Example 4

A 3.5 g capsule containing 60% of 70% DHA-oil, optionally containing 10% by weight 1-stearoyl, 2-docosahexaenoyl phosphatidylcholine (SDHPC), three per day.

Example 5

A 4 g capsule containing 60% of 50% DHA-oil, 10% SDHPC and 5% an anti-cancer regular drug (e.g. taxol, doxorubicin or cis-platinum), eight per day.

Example 6

Parenteral pharmceutical compositons in a fluid form are prepared using conventional standard procedures in agreement with the physical duty behaviour and stability of active materials used. For instance, a colloidal fluid for parenteral administration containing in each 5 ml, 2 g of 40% DHA-oil, is stabilized and can be given 10 ml daily.

Example 7

A fluid for parenteral administration containing 60% of 50% DHA-oil, 20% by weight DHA-containing phospholipid (e.g. 1-stearoyl, 2-docosahexaenoyl phosphatidyl choline: SDHPC), optionally containing 5% by weight of a regular anti-cancer drug (e.g. taxol, doxorubicin and cisplatinum) is prepared and stabilized and can be administered, 5 ml for two times daily.

EVALUATION OF A DHA-RICH PREPARATION IN THE PC-3M HUMAN PROSTATE CANCER MODEL

The efficacy of a DHA-rich oil (DHASCO), fed at a single level, in suppressing the growth and metastasis of PC-3M human prostate cancer cells injected the orthotopically into male athymic nude mice is determined using the model described below.

The PC-3M metastatic model for human prostate cancer using orthotopic implantation in nude mice was developed by Fidler and coworkers, and described in *J. Natl. Cancer Inst.* 84, 951–957 (1992).

The diets are based on those employed in the study regarding the effect of dietary menhaden oil (MO) on MDA-MB435 human breast cancer cell growth and metastasis in nude mice as described in *J. Natl. Cancer Inst.* 85, 1743–1747 (1993).

Applicants have chosen the following 4 dietary groups, with 20 mice per group:
 (1) Low-fat: 5% (wt) corn oil (CO)
 (2) High-fat: 18% MO: 5% CO (wt/wt)
 (3) High-fat: 18% DHASCO: 5% CO
 (4) High-fat: 18% DHASCO: 5% (SDHPC): 5% CO (wt/wt/wt)

The mice are assigned to the 4 groups in a manner to ensure similar body weight ranges in each group at the start of the experiment. The diets are started 7 days before the intraprostatic injection of $5 \times 10^5$ PC-3M cells, after which the mice are weighted and palpated at weekly intervals. After a 6 week observation period, the mice are killed by cervical dislocation, full necropsies performed, primary tumors and grossly visible metastases weighed and measured, and tissues taken, as indicated, for histological examination.

The end point comparisons are as follows:
 (1) Weight and size of intraprostatic tumors (typically, after 6 weeks these weight 0.35±0.20 g; the normal mouse prostate weights 0.050)
 (2) Combined weight of intra-abdominal lymph node metastases.
 (3) Presence of macroscopic hepatic metastases.
 (4) Presence and extent of micrometastases in lungs and abdominal organs.

Applicants' results are that the Ψ-3 fatty acid-rich diet suppresses intraprostatic cancer growth and metastases compared with the tumor progression observed in the 5% CO-fed group of mice. Subgroup comparisons would be 18% MO: 5% CO versus 5% CO, 18% DHASCO: 5% CO versus 5% CO, and 18% MO: 5% CO versus 18% DHASCO: 5% CO and 18% DHASCO: 5% CO versus 18% DHASCO: 5% SDHPC: 5% CO.

TREATMENT MODALITIES FOR LUNG CANCERS BASED ON DHASCO OR A DHASCO-DERIVED DHA-CONTAINING PHOSPHOLIPID

The present experiments are carried out to demonstrate the in vivo anti-cancer activity of DHASCO and/or DHASCO containing 1-stearoyl-2-docosahexaenoyl-3n-glycero-phosphocholine (SDHPC). A Lewis lung carcinoma (LL/2) cell line is used as model system in a two-tiered set of experiments.

(1) In vitro and in vivo experiments are performed with DHASCO to elucidate its uptake by Lewis lung carcinoma (LL/2) cells in culture. DHASCO-based feeding experiments in syngeneic mice are undertaken to assess their effectiveness and compare the outcome with menhaden oil feeding experiments. These feeding experiments were effective in murine leukemia caused by intraperitoneally-inoculated T27A leukemia cells. If necessary, DHASCO will be transesterified, purified and used to prepare SDHPC, which is known to have antileukemic activity in mice.

(2) In vivo experiments are performed to assess anti-Lewis lung carcinoma activity of DHASCO or DHASCO containing SDHPC by spraying directly into the airways of mice, or by feeding the mice as part of their regular dietary intake. In order to grow tumors of LL/2 cells, they are implanted into the kidneys of syngeneic mice. The tumors formed are allowed to metastasize to the lung. One control group of twenty mice, implanted but untreated, will be compared with another group of twenty mice treated at an optimal dose level of DHASCO or DHASCO containing SDHPC in aerosol. An additional treatment group will provide data on the effects of dietary supplementation of DHASCO.

The endpoints are as follows:

(a) Metastasized tumor nodule formation and distribution analysis in the lung. Ten mice from each group are sacrificed and the above nodule analysis performed. In addition, in order to assess anti-metastasis effects of DHASCO or derivatives, the most successful treatment modality is administered to a group of twenty mice from the time of the initial LL/2 cell implantation.

(b) Survival data in terms of death endpoint are analyzed.

What applicants' desire to claim is as follows:

1. A pharmaceutical composition comprising enhanced effective amounts of: (a) a carrier based on a glyceridic oil having as its main constituent 15% to 100% by weight of docosahexaenoic acid based on the total fatty acid content and (b) an antineoplastic drug selected from the group consisting of cis-platinum, doxorubicin, taxol, bleomycin sulfate, rifamycin, busulfan, chlorambuck, cyclophosphamide, mechlorethamide hydrochloride, melphalan, pipobroman, thiotepa, uracil mustard, cytarabine, fluorouracil, floxuridine, mercaptopurine, methotrexate, thioguanine, dacarvazine, hydroxy-urea, mitotane, procarbazine hydrochloride, quinacrine hydrochloride, vinblastine sulfate, vincristine sulfate, methyltestosterone, testosterone, megestrol and hydroxyprogesterone.

2. A pharmaceutical composition comprising enhanced effective amounts of: (a) a glyceridic oil having as its main constituent at least 27% by weight of docosahexaenoic acid of the total fatty acid content and (b) taxol.

3. A pharmaceutical composition comprising enhanced effective amounts of: (a) a carrier based on a glyceridic oil having as its main constituent 15% to 100% by weight of docosahexaenoic acid based on the total fatty acid content and (b) an antineoplastic drug.

4. The composition of claim 3 in the form of a parenteral pharmaceutical composition.

5. The composition of claim 3 wherein said antineoplastic drug is taxol.

* * * * *